United States Patent [19]

Schroeder et al.

[11] Patent Number: 4,893,513

[45] Date of Patent: Jan. 16, 1990

[54] METHOD AND APPARATUS FOR BOND TESTING

[75] Inventors: Joseph G. Schroeder, Bay Village; Jan L. Shanaberger, Westlake; William R. Rehman, Vermilion; Harry J. Lader, Lakewood; Jeffrey S. Noss, Bay Village, all of Ohio

[73] Assignee: Nordson Corporation, Westlake, Ohio

[21] Appl. No.: 265,719

[22] Filed: Nov. 1, 1988

[51] Int. Cl.$^4$ .............................................. G01N 3/08
[52] U.S. Cl. ..................................... 73/827; 73/150 A
[58] Field of Search ...................... 73/827, 150 A, 827

[56] References Cited

U.S. PATENT DOCUMENTS

| | | | |
|---|---|---|---|
| 3,253,461 | 5/1966 | Blanchard et al. | 73/150 A |
| 3,580,065 | 5/1971 | Strittmater et al. | 73/827 X |
| 4,637,252 | 1/1987 | Rhee et al. | 73/150 A |

Primary Examiner—Jerry W. Myracle
Attorney, Agent, or Firm—Wood, Herron & Evans

[57] ABSTRACT

In an apparatus and method for measuring the strength of an adhesive bond, a dispenser applies adhesive to a substrate for a prescribed period of time, a conveyor moves the substrate to a compressing station within a preselected open time, after which time a compressor compresses the substrate against another substrate to form an adhesive bond therebetween, the bond being formed under a substantially constant compression force and for a preselected compression time. During the latter portion of the compression time, the bonded substrates are moved together at a substantially constant rate of speed through a transition distance, one of the substrates contacting a stop plate at the end of the compression time to prevent further movement while the other of the substrates continues at the substantially costant rate of speed to break the bond. A load cell measures the maximum pull force required to break the bond and also provides a real time analog signal for the pull force of the bond during tension, thereby to obtain an indication of the total energy expended in breaking the bond.

25 Claims, 3 Drawing Sheets

METHOD AND APPARATUS FOR BOND TESTING

FIELD OF THE INVENTION

This invention relates to a method and apparatus for measuring the properties of an adhesive bond formed between two substrates.

BACKGROUND OF THE INVENTION

For the purposes of this application, a bond between two substrates or container laps is the mechanism that holds the substrates together and resists the separation of the substrates when subjected to forces perpendicular to the plane of the substrate. Bond strength is the ultimate separation force that the bond can resist after the adhesive is set or cured. Green strength is the ultimate separation force that the bond can resist at a given time prior to final curing or setting of the adhesive.

In the field of closing containers such as boxes, cases, cartons, etc., with an adhesive, it is important to limit open time in order to avoid drying or setting up of the adhesive before the flaps are closed. At the same time, the adhesive must provide sufficient early strength, or green strength, shortly after the flaps are closed in order to prevent popping apart once the closing force has been removed.

Adhesives used in closing containers vary in final bonding strength and in green strength. For instance, a cold glue adhesive generally requires about 10-30 seconds to achieve sufficient early strength to prevent popping apart of the flaps. A typical hot melt adhesive requires under three seconds and sometimes less than one second in order to achieve sufficient early strength.

Primarily due to greater early strength, hot melt adhesives are generally preferred over cold glue adhesives for assembly line closing of containers. However, under some circumstances a cold glue adhesive may be substituted for a hot melt adhesive if it is known that the substituted adhesive can provide sufficient early strength within the prescribed time limit. To determine whether or not a particular adhesive would be suitable for a desired purpose, and to enable optimization of assembly line container closing, it is desirable to compare the bonding properties, particularly the green strength, of various adhesives on an accurate and repeatable basis.

Present bond testers provide some useful data for comparing the performance properties of adhesives by measuring the force required to pull apart two adhesively bonded substrates. Two well known bond testers measure the strength required to break a bond between two substrates when the bond is placed in tension under a constant force. A strain gauge or an equivalent measuring device provides an indication of the bond's resistance to the applied constant force at the point in time when the bond fails.

Although a bond tester of this type can provide comparative data of some value in assessing relative bond strength when the measured strengths of the adhesive are fairly close, such a bond tester does not provide sufficient comparative data for adhesives which have a wide range in bond strength. An adhesive bond under tension will initially resist the force of tension to some degree, thereby slowing the rate at which the substrates are pulled apart to break the bond. Therefore, despite the application of a constant pull force, the rate at which the substrates are pulled apart varies appreciably. As the difference in bond strengths between two adhesive bonds increases, the difference in the rates at which the substrates are pulled apart to break the bonds also increases.

Thus, while some indication of the strength of a bond can be obtained with a bond tester of this type, the obtained value is not particularly useful for comparative purposes. In short, the application of a constant force to break an adhesive bond does not in and of itself provide adequate comparative performance data for evaluating the relative bond strengths of adhesives on an equal basis. Moreover, the bond testers of this type do not provide any measure of the total work expended during tension to break the bond.

In another type of bond tester, two substrates are bonded together with an adhesive at a first location. After a sufficient time has elapsed for the bond to achieve final strength, the bonded substrates are transferred to a second location whereupon the bond strength of the bond is measured while moving a wire rod laterally at a constant rate of speed between the two substrates to effect a failure of the bond.

Although a device of this type may be used to obtain comparable final strength measurements for various adhesives, it is not suitable for use in obtaining measurements of the green strength of an adhesive bond, i.e., the strength of the bond shortly after compression is applied but before final strength is achieved. A device of this type does not provide data sufficient to indicate whether or not a particular adhesive will provide a bond of sufficient strength within a prescribed short time limit. Moreover, this type of device does not measure the tensile strength of the bond, the force required to pull the bond directly apart. It is more in the nature of a peel tester, testing the peel strength of an adhesive bond.

SUMMARY OF THE INVENTION

It is an object of the present invention to provide a bond tester which is capable of producing bond performance data for an adhesive which can be readily and accurately compared with the bond performance data of a wide variety of adhesives, thereby to facilitate the determination of whether or not the adhesive can be used under prescribed conditions.

The present invention is predicated in part upon the concept of providing a bond tester in which two substrates are joined by an adhesive and are subsequently pulled apart at a constant pull rate while measurements are made of the pull force. In accordance with the present invention the substrates are pulled apart in a direction normal to their plane of contact so that a pure tension force, not a peeling force is applied to the bond.

To this end, a bond testing apparatus according to a preferred embodiment of the invention includes a dispenser, a conveyor, a compression cylinder, a programmable controller, a vertically movable tension head, a stop plate and a load cell. The dispenser applies an adhesive to be tested to a first substrate at a dispensing station. The conveyor transports the first substrate from the dispensing station to a compressing station within a preselected open time. A tension head mounted above the compressing station holds a second substrate. The compression cylinder raises the first substrate into contact with the second substrate, compressing the substrates to form an adhesive bond under a preselected, substantially constant compressive force during a compression time period. During a latter portion of the compression time period, determined by the controller, the tension head raises the bonded substrates upwardly at a substantially constant rate of speed, with the compression cylinder continuing to apply upwardly directed force to compress the bond. After the substrates have traveled through a transition distance, within which distance the tension head has accelerated to full speed, a stop plate engages and prevents further upward movement of the first substrate. The tension head continues upwardly with the second substrate at a substantially constant rate of speed to break the adhesive bond. The load cell is connected to the tension head and measures the maximum pull force required to break the bond.

The load cell also provides a real time analog signal of the compression force and the pull force during the compression and the tension cycles, respectively, on the bond. By integrating pull force multiplied by velocity for the time period during which the bond is under tension, a value can be obtained for the total work expended in breaking the bond.

In order to determine the precise point in time during compression when the tension head should be raised, the known time it will take for the tension head to travel through the transition distance (e.g., for a given raising speed) is subtracted from the preselected compression time period to obtain a stationary compression time. At the end of the stationary compression time, the controller initiates raising of the tension head. Thus, compression occurs during a stationary compression time when the substrates do not move vertically and during a moving compression time, when the bonded substrates are raised together through the transition distance. Compression ends when the bottom substrate contacts the stop plate.

To facilitate comparison of adhesive bond strength, a printer records pertinent information such as gun-on time, open time, compression time, compression force and bond force for each test. These values may also be displayed on a control panel. Preferably, the control panel also provides selectable controls for preselecting the constant compressive force to be applied to form the bond, the open time period, the compression time period and appropriate start and stop pushbuttons.

A bond testing method according to a preferred embodiment of the invention comprises the steps of: applying an adhesive to a first substrate; after the lapsing of an open time period of preselected duration, compressing the first substrate to another substrate under a constant compression force for a compression time period of preselected duration to form an adhesive bond therebetween; pulling one of the substrates from the other substrate at a substantially constant rate of speed to break the bond; and, measuring the maximum pull force of the bond during the withdrawing step. The bond tester of this invention enables all of these steps to be performed within about one second.

The bond tester provides accurate and repeatable values for the bond strength of an adhesive bond formed under a selected substantially constant compressive force during a preselected compression time period. This is achieved by pulling the bond apart at a constant rate of speed with the stop plate providing an immediate transition between compression of the bond and tension of the bond. The obtained bond performance data for a particular adhesive can be readily compared with data obtained for other types of adhesive. Thus, hot melt and cold glue adhesives can be compared on an equal basis.

For a particular adhesive to be tested, and for a desired compression force, a plot of compression time versus maximum strength can be obtained by running a number of tests for a variety of different compression times. This enables an operator to determine how long compression must be applied to obtain a bond of the desired strength for that particular adhesive. Additionally, with the other parameters constant, open time may be varied over a number of tests in order to provide a plot of maximum bond force versus open time. This enables a determination of whether or not a particular adhesive provides sufficient bonding strength within an allotted open time.

The bond tester of this invention can easily be adapted to a wide variety of adhesives and substrates for a number of other industries such as the automotive industry, bookbinding or furniture making.

One advantage of the present bond tester is that it enables a bond to be made, compressed and pulled apart in a continuous operation on a single device. Moreover the present tester provides an immediate transition from compression to tension of the bond. Additionally, the present tester makes possible short cycle times.

These and other objects and advantages of the invention will be more readily appreciated in light of the following detailed description and the drawings in which:

DETAILED DESCRIPTION OF THE DRAWINGS

FIGS. 1,2, 3 and 4 depict a bond tester 10 for testing the bond strength of an adhesive 12 according to a preferred embodiment of the invention. A first substrate 13 is transported by a conveyor 16 through a dispensing station 17 where the adhesive 12 is dispensed on a top surface thereof. The conveyor may be driven by a motor 19 controlled by a conveyor motor controller 20. The substrate may be placed on the conveyor 16 either automatically or by hand.

The substrate 13 may be of any desired substrate material, but preferably is of the same material that will be used in the operation for which the adhesive is being tested. One typical substrate that may be used with this bond tester 10 is a single fluted corrugated paperboard approximately 0.156" thick, preferably about 8 inches long and 5 inches wide. The width of the substrate 13 is the dimension which extends transverse the longitudinal direction of the conveyor 16, and the length of the substrate 13 is the dimension directed along the longitudinal direction of the conveyor 16.

Figure 1:
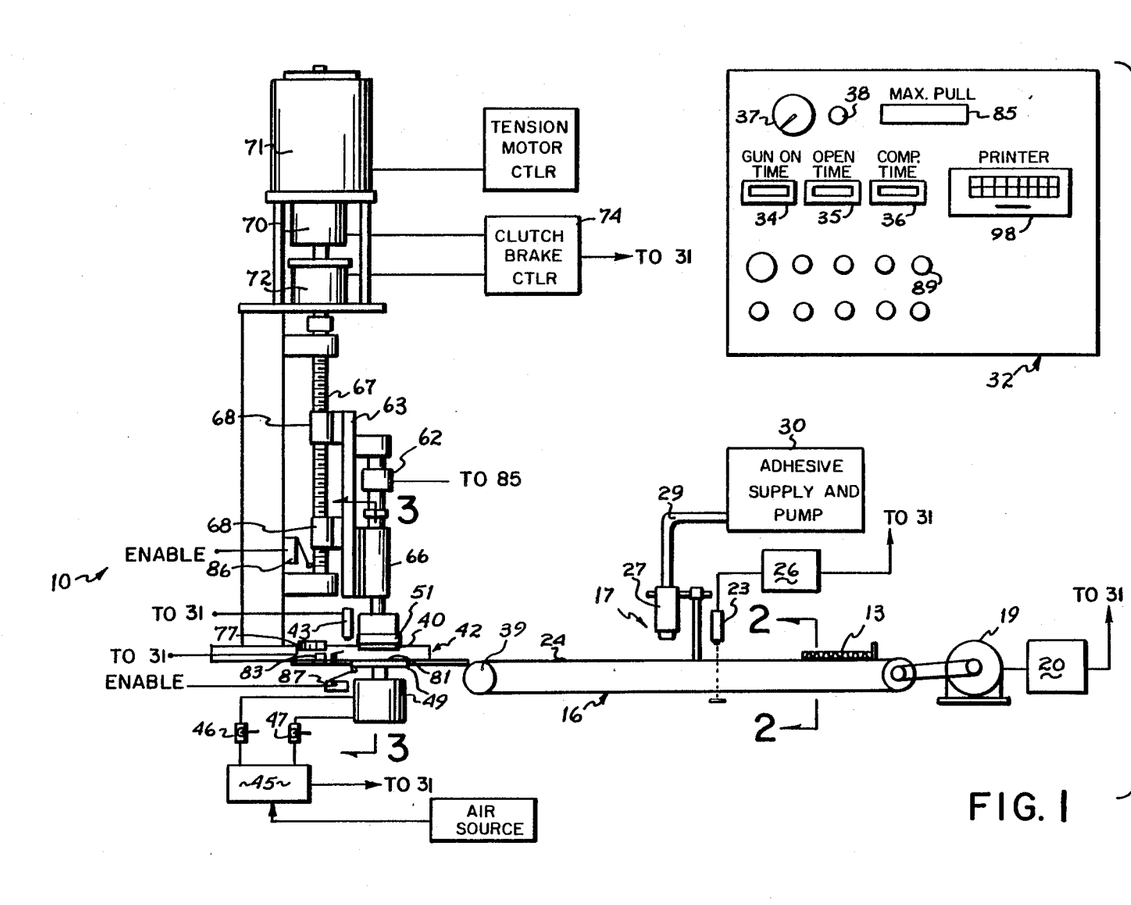
FIG. 1 is a front view, partially schematic, of a bond testing apparatus according to a preferred embodiment of the invention.
Figure 2:
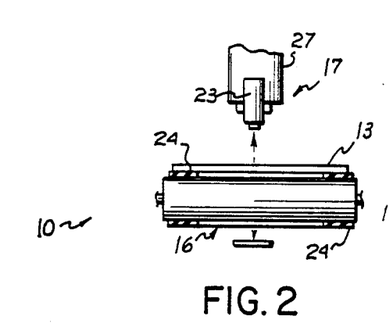
FIG. 2 is a sectional view taken along lines 2—2 of FIG. 1.

Mounted upstream of the dispensing station 17, a trip sensor 23, preferably a photoelectric sensor utilizing both a transmitter and a receiver, is located above the conveyor 16 and directed downwardly to detect the presence of substrate 13 as it moves toward the dispensing station 17. Alternatively, the trip sensor may comprise a photo cell above the conveyor 16 directed downwardly and aligned with a light sensor below the conveyor 16 directed upwardly to detect substrate 13. As shown in FIG. 2, the conveyor 16 includes two endless belts 24 spaced close enough to carry the substrate 13 but sufficiently far apart so as to not be detected by the sensor 23. The trip sensor 23 signals a controller 26 to activate a dispenser 27, or glue gun, to dispense adhesive 12 on a top surface of the substrate 13. The spacing of the belts 24 also prevents accidental dispensing of adhesive 12 upon the conveyor 16.

Adhesive 12 is dispensed on substrate 13 to provide a single bead about $\frac{1}{8}''$ to 3/16" in width and at least one inch in length, the length of the bead extending parallel to the belts 24. Adhesive 12 is fed to the gun 27 via a conduit 29 connected to an adhesive supply and pump assembly 30. The supply/pump 30 is periodically filled with liquid adhesive by an operator. If hot melt adhesive is used, it may be supplied in solid form and then melted into a liquid state. The glue gun 27 may be mounted in any desired manner above the dispensing station 17.

The sensor 23 senses the substrate 13 and the gun 27 is turned on for a preset dispense cycle. Preferably, a programmable controller 31 (not shown), such as an Allen Bradley PLC 2/02 is mounted behind a control panel 32 and provides all timing controls for the bond tester 10. The controller 31 is connected to gun controller 26 to control elapsed time during dispensing. The desired dispensing time is selected on dial 34 on the control panel 32, under the designation "GUN-ON TIME". A typical gun on time is about 0.1 seconds.

The control panel 32 provides a rotatable dial 35 to enable selection of an open time period for the adhesive 12. The selected open time period commences upon completion of the dispensing operation and continues until substrate 13 is in position to be bonded with another, second substrate 40 at a compressing station 42. Typically, conveyor 16 transports adhesive laden substrate 13 to the compressing station 42, about 8" to 12" away, at a speed of about 150 feet per minute, or well within most preselected open time periods, time periods which usually extend from about 1 second to about 3 seconds. The controller 31 also controls elapsed open time.

The conveyor 16 is capable of operating at a speed of about 300 feet per minute, which would transport substrate 13 from the dispensing station 17 to the compressing station 42 within about 0.2 seconds.

At the end 39 of the conveyor 16, the substrate 13 has enough linear momentum to be propelled to the compressing station 42, under the second substrate 40. A position sensor 43 provides a signal to controller 31 to indicate that substrate 13 has arrived at the compressing station 42. The signal is relayed to the compression control valve 45 which directs the airflow through valves 46 and 47 to either raise or lower a compressor 49, preferably a compression cylinder located beneath the substrate 13. Upon detection of the presence of substrate 13, and after lapsing of the preselected open time period, compression cylinder 49 is actuated to raise the adhesive-laden substrate 13.

Figure 3:
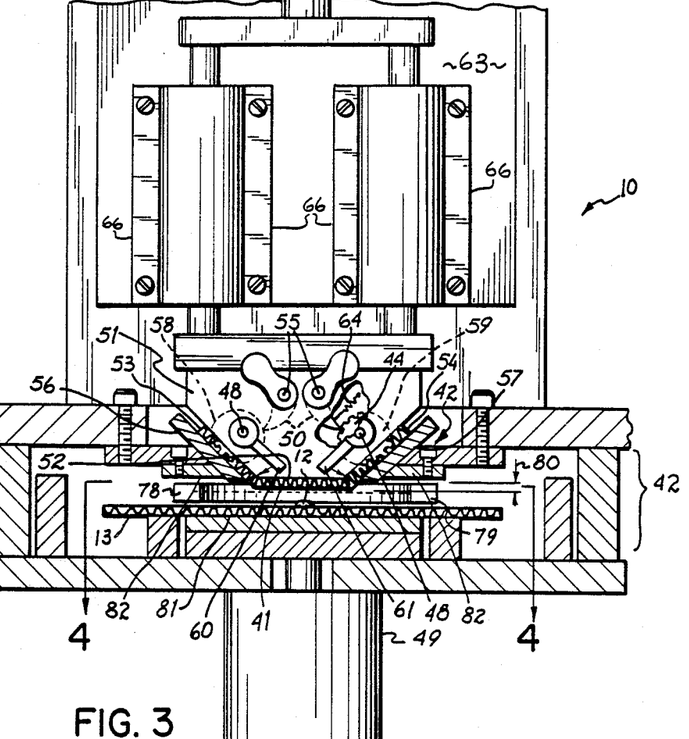
FIG. 3 is a sectional view taken along lines 3—3 of FIG. 1.

Above the compressing station 42, a second substrate 40 is carried by a vertically movable tension head 51. As shown in FIG. 3, the substrate 40 is held by tension head 51 so as to place a midportion 41 thereof, which resides between end portions 53 and 54, firmly against a bottom surface 52 of the tension head 51 during the compression and tension cycles. Firm securement of midportion 41 to bottom surface 52 is critical to the obtaining of accurate test results. Otherwise, if slipping of midportion 41 away from bottom surface 52 should occur, there will be an undesired time lag between compression and tension on the bond.

To accomplish firm securement of substrate 40 to the tension head 51, end portions 53 and 54 of the second substrate 40 are wedged between angle plates 56 and 57. Eccentric cams 58 and 59 have circumferential gripping teeth to clamp and engage the end portions 53 and 54 and pull midportion 41 tightly against bottom surface 52 when rotatable handles 60 and 61 are turned outwardly, as shown by the directional arrows in FIG. 3. Each of the cams 58 and 59 has a ratchet and pawl mechanism associated therewith to prevent inward rotation of the handles 60 and 61, respectively, and thereby maintain clamped tension on the substrate 40 during compression and tension on the bond.

Because the ratchet and pawl mechanisms are mirror images of each other, preventing outward handle rotation, only the ratchet and pawl mechanism associated with cam 59 will be described. A ratchet wheel 44 aligned along a cam axis 48 but displaced rearwardly (as viewed in FIG. 2) from toothed cam 59 is engaged by a pawl 50. The pawl 50 is pivotal in a clockwise direction about a pawl axis 55 to permit outward, or counterclockwise, rotation of cam 59 when handle 61 is turned outwardly. To rotate handle 61 counterclockwise, the pull force of a tension spring 64 connected to the pawl 50 must be overcome. The spring 64 is held at its other end by an interior side wall (not shown) of the tension head 51. The tension spring 64 biases the pawl 50 back into engagement with the next ratchet of the ratchet wheel 44. Engagement between the ratchet wheel 44 and the pawl 50 prevents clockwise rotation, or loosening, of cam 59 upon end portion 54. Similarly, another ratchet and pawl mechanism prevents outward, or counterclockwise loosening of cam 58 from end portion 53.

The ratchet and pawl mechanisms retain the cams 58 and 59 in clamped engagement with end portions 53 and 54. This assures that the bond will be broken in a vertical direction, perpendicular to the plane of engagement of the substrates, and that the test will provide a measure of green strength and not peel strength.

A load cell 62 connects tension head 51 to a vertically movable slide 63. The load cell 62 senses vertical force, directed either upwardly or downwardly, upon the tension head 51. The tension head 51 is further connected to slide 63 by a ball bushing guide 66, to constrain all but vertical movement of the tension head 51 and ensure that load cell 62 will sense only vertically directed force.

Slide 63 is mechanically coupled to a vertically disposed, rotatable ball screw 67 by ball nuts 68, and can be vertically raised or lowered by rotation of the ball screw 67. A clutch 70 couples and decouples a constant speed reversible motor 71 to ball screw 67 when vertical motion of slide 63 is desired. A brake 72 holds the slide 63 in position when vertical motion of slide 63 is not desired. Clutch 70 and brake 72 are controlled by a clutch/brake controller 74. Preferably a motor 71 of about 0.25 hp runs continuously at a speed of about 300 revolutions per minute. Coupled at a one to one gear ratio to the ball screw 67, rotation of the motor 71 rotates ball screw 67 at about 300 revolutions per minute. This raises slide 63 at a substantially constant rate of speed of about 1" per second with about 170 pounds of upwardly directed lifting force.

After the compression controller 45 has been signalled by controller 31 that the open time period has lapsed, and by sensor 43 that substrate 13 has been detected at the compression station 42, the compression controller 45 actuates the compression cylinder 49 to raise substrate 13 into contact with substrate 40.

Figure 4:
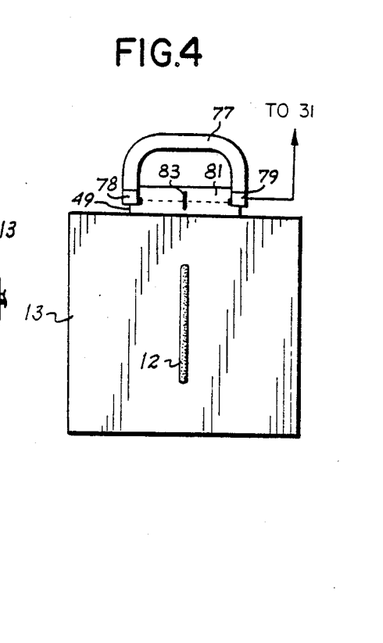
FIG. 4 is a sectional view taken along lines 4—4 of FIG. 3.

A position indicator 77 adjacent the compressing station 42 signals the controller 31 to initiate running of the preselected compression time upon sensing contact between the substrate, or upon detecting a top portion 81 of the cylinder 49 at about the time that the substrates begin compressing the adhesive 12. Preferably, as shown in FIG. 4, position indicator 77 has a U-shape, with a transmitter 78 mounted at one leg to transmit a signal horizontally, just below substrate 40, toward a receiver 79 located at the other leg. A flag 83 mounted to top portion 81 raises with the cylinder 49 to interrupt the horizontally directed signal at about the time that the substrates begin compressing the adhesive 12. Depending upon the thickness of substrate 40, the vertical position of sensor 77 may require adjustment.

Preferably, the control panel 32 also provides rotatable controls 36 and 38 that enable an operator to select the desired length of compression time and the compression force, respectively. The selected piston pressure is displayed on dial 37 and can be varied by rotating dial 38, while the actual measured compression force from the load cell 62 is displayed on meter 85. Dials 37 and 38 are operatively connected to compression controller 45 via controller 31. The compression time period commences when compressive force is initially applied to the adhesive 12 by substrates 13 and 40, as sensed by indicator 77. The selected compression time may range from about 0.2 seconds up to 99 seconds, during which time the preselected compressive force is applied in a substantially constant manner to the substrates to form an adhesive bond therebetween. A typical value of compression force for a bond tester of this type would be between 0.5 pounds to 10 pounds.

During a latter portion of the compression time period, controller 74 actuates clutch 70 to couple motor 71 to ball screw 67. Rotational movement of ball screw 67 raises slide 63 via a ball nut 68 to raise tension head 51 at a substantially constant rate of speed. The adhesively bonded substrates 13 and 40 are raised upwardly together through a transition distance 80 as compression cylinder 49 continues to apply compression, thus minimizing the effects on the bond of initial upward acceleration of slide 63 as 71 is coupled. For a tension head moving upwardly at about 1" per second, a transition distance or zone of about 0.040" has proved suitable.

To determine when the clutch/brake controller 74 should be actuated to couple motor 71 to ball screw 67, the controller 31 subtracts the known time required for travel through the transition distance 80 from the preselected compression time to obtain an initial, stationary, compression time, which is stored in a stationary compression timer in the controller 31. The initial compression time commences upon sensed contact between the substrates by sensor 77. After lapsing of the stationary compression time, the controller 31 signals the clutch brake controller 74 to couple motor 71 to ball screw 67.

As shown in FIG. 3, stop plates 82 are situated above the transition distance 80 to engage substrate 13 on opposite sides of the adhesive 12 and prevent further upward movement. For this reason, bottom substrate 13 must be of sufficient width to engage both plates 82. After engagement of substrate 13, tension head 51 and substrate 40 continue upward travel at a substantially constant rate of speed to break the adhesive bond.

The load cell 62 measures the maximum pull force required to break the adhesive bond. Because the ball bushing guide 66 ensures that tension head 51 transmits only vertical forces to the load cell 62, a pure tensile strength of the bond will be measured as the top substrate 40 is pulled directly away from bottom substrate 13. Although any one of a variety of load cells 62 could be utilized with this invention, a Sensotech Model 31 which measures a range of ±25 pounds of load force coupled to a Sensotech Model 450D Amplifier and Display Unit has proved suitable. An internal electronic peak hold circuit in the amplifier captures the peak pull force required to break the bond. A BCD output option, which is available for the Sensotech Model 450D load cell amplifier unit, provides a digital signal of maximum measured pull force which can be input to controller 31 and displayed on the digital display 85 and can be printed out by printer 98.

The load cell amplifier also provides a real time analog output signal for the pull force of the bond during tension. By inputting this signal to an oscilloscope or a data acquisition system, a graphical representation of pull force versus time can be obtained, the area under the curve from initial tension to breaking of the bond providing an indication of the total energy expended in breaking the bond. By substituting the known constant velocity of the tension head and substituting a function having characteristics similar to the graphical representation of measured pull force, the measured pull force times the constant velocity can be integrated for the period of time during which the bond was under tension to provide a value for the total work expended in breaking the bond.

This structure provides an immediate transition between substantially constant compression on the bond and tension on the bond, with tension provided at a substantially constant rate of speed to enable accurate and repeatable bond strength data to be obtained for a given adhesive. By testing a variety of adhesives with this bond tester, comparison of bond strengths and other properties can be assessed with respect to many variables such as adhesive bead size, open time, compression time, compression force, maximum measured pull force and work expended in breaking the bond.

Figure 5:
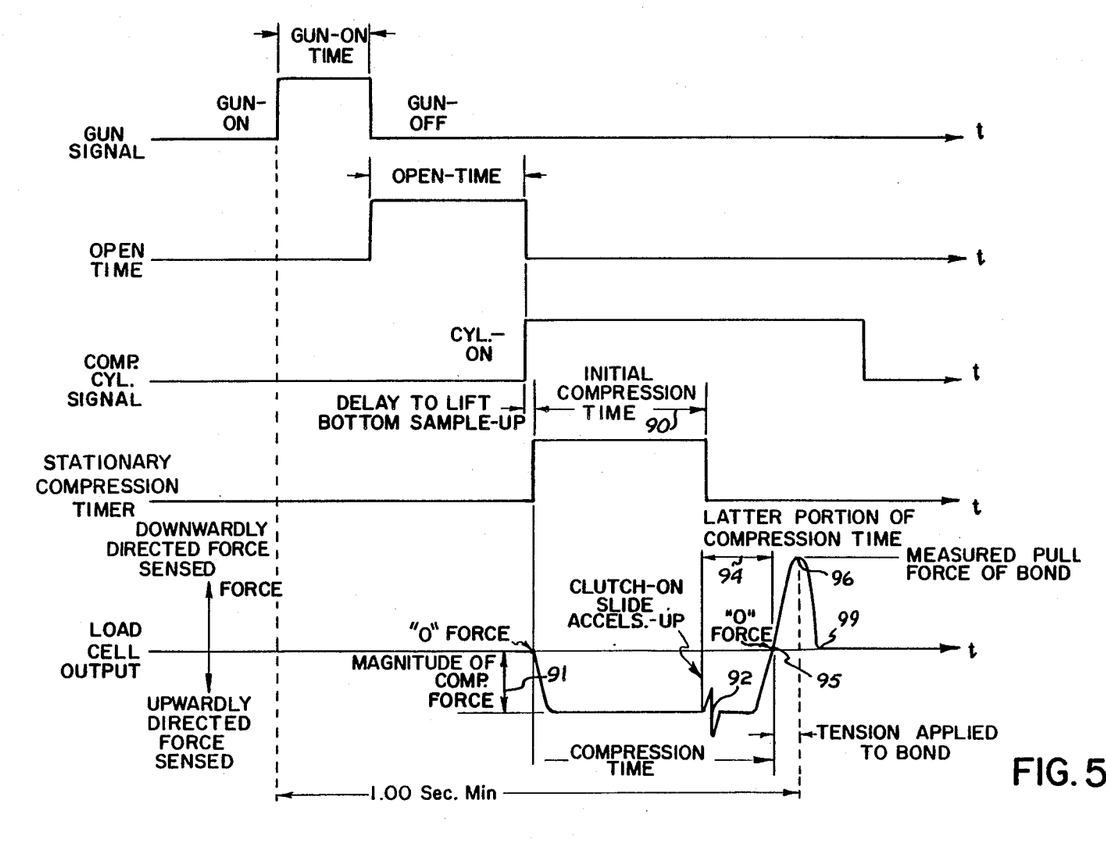
FIG. 5 is a timing diagram for a bond testing apparatus according to a preferred embodiment of the invention.

A sequence of operations for this bond testing apparatus can be understood with reference to the timing diagram of FIG. 5. Initially, substrate 40 is loaded into tension head 51. Sample substrate 13 is placed on conveyor 16. The adhesive 12 to be tested is placed in the adhesive reservoir 30. The operator uses dials 34, 35, 36 and 38 on control panel 32 to select gun on time, an open time, a compression time, and a compression force, which are input to and stored by the controller 31. The controller 31 computes the stationary compression time for a known motor speed and transition distance 80. An indicator 86 adjacent to ball screw 67 provides an enabling signal to indicate that slide 63 has positioned tension head 51 and substrate 40 at the compressing station 42. Another indicator 87 provides an enabling signal to indicate that compression cylinder 49 is in the fully retracted position and is ready to be raised.

Depressing a start pushbutton 89 at the control panel 32 activates controller 31 to turn on conveyor controller 20 and conveyor 16 to carry sample 13 toward dispensing station 17. Sensed presence of the substrate 13 provides a signal to the gun 27 to dispense adhesive 12. The adhesive is dispensed for a preselected time. Once dispensing is completed, the controller 31 initiates running of the preselected open time period, within which time period the adhesive laden substrate 13 is transported by the conveyor 16 to the compressing station 42.

When substrate 13 arrives at the compressing station 42 and the open time has elapsed, compression cylinder 49 raises substrate 13. After raising the compression cylinder 49 to a vertical level such that flag 83 is detected by indicator 77, i.e., about the time that substrate 13 contacts substrate 40 with adhesive 12 therebetween, the controller 31 initiates running of the compression time period. Upon contact, a substantially constant compressive force is applied to the substrates to form an adhesive bond therebetween.

During the initial stage of the compression time period designated 90 in FIG. 5, the upwardly directed force against the tension head 51 will be sensed by the load cell 62 as a negative force of the preselected magnitude, as shown at 91 in FIG. 5. The sensed compression force will be displayed at 85. After the initial compression time has elapsed, controller 31 signals controller 74 to actuate clutch 70. This couples motor 71 to ball screw 67 and vertically raises tension head 51 together with the substrates at a rate of about 1" per second. Movement of the substrates will result in a short transient change of force being sensed by the load cell 62, as shown at 92 in FIG. 5. However, the applied compression force during the compression time will remain substantially constant at the selected value.

Raising of the substrates in bonded relationship continues unobstructed through a transition distance 80 for a time period designated as 94 in FIG. 5, until substrate 13 contacts the bottoms of plates 82 to prevent further upward movement. Immediately after engagement of substrate 13 as shown at 95, force sensed by the load cell 62 will become downwardly directed, or positive, as raising of slide 63 places upward vertical tension on the bond. Tension head 51 continues to vertically withdraw substrate 40 from substrate 13 at a substantially constant rate of speed to break the bond, typically within about 100 milliseconds.

A peak pull force of the bond, shown at 96 in FIG. 5, is measured by the load cell 62 for display on screen 85 at control panel 32. During tension on the bond, the maximum sensed tension is increasing at such a high rate that the corresponding display of maximum measured tension 85 cannot keep up with it. However, after the bond has broken, screen 85 will hold and display the maximum measured downwardly directed force. A typical value of force required to pull apart an adhesive bond formed from a single bead having a width of about an ⅛" to 3/16" would be about 12-13 pounds. Preferably, gun on time, open time, compression time, compression force and maximum bond force are recorded by the controller 31 and input to a line printer 98, mounted on panel 32.

While the above description of a method and apparatus for testing bond strength constitutes a preferred embodiment of the invention, it is to be understood that the invention is not limited thereby and that in light of the present disclosure of the invention, various other alternative embodiments will be apparent to one of ordinary skill in the art. Accordingly, it is to be understood that changes may be made without departing from the scope of the invention as particularly set out and claimed.

We claim:

1. An apparatus for measuring the strength of an adhesive bond between two substrates comprising:
   a dispenser adapted to supply an adhesive to a first of said substrates;
   compressor means adapted to apply compressive force between said first substrate and a second substrate for a preselected compression time to form an adhesive bond therebetween;
   means for pulling one of said adhesively bonded substrates from the other of said substrates at a substantially constant rate of speed to break said adhesive bond; and
   a load cell operatively associated with said pulling means adapted to measure the force applied to said adhesive bond.

2. The apparatus of claim 1 in which said substrates engage one another on a plane, and said pulling means pulls in a direction substantially perpendicular to said plane of engagement of said substrates.

3. The apparatus of claim 1 in which said load cell measures the maximum pull force required to break said adhesive bond.

4. The apparatus of claim 1 wherein said compressor means and said pulling means cooperatively move said substrates in bonded relationship through a transition distance during a portion of said preselected compression time period, said pulling means further comprising:
   a stop plate adapted to engage and prevent further movement of the other of said substrates at the end of said compression time period.

5. The apparatus of claim 1 wherein said compressor means and said pulling means cooperatively move said substrates in bonded relationship through a transition distance during a portion of said preselected compression time period, and further comprising:
   a controller operatively associated with said compressor means to initiate application of compressive force to said substrates after an open time period of preselected duration has elapsed, said open time period commencing upon the completion of dispensing said adhesive, said controller also initiating movement of said pulling means.

6. The apparatus of claim 5 wherein said load cell measures a maximum pull force required to break said adhesive bond and further comprising:
   means operatively associated with said controller and said load cell for displaying said maximum measured pull force, said preselected open time period, and said preselected compression time period.

7. The apparatus of claim 6 wherein said compressor means applies a preselected substantially constant compressive force during said compression time period, and further comprising:
   means for recording said maximum measured pull force, said preselected open time period, said preselected compression time period, and said preselected compression force.

8. The apparatus of claim 1 wherein said load cell also provides a real time analog output signal for the pull force of the bond during tension, whereby said signal may be utilized to obtain an indication of the total work expended in breaking the bond.

9. An apparatus for measuring the strength of an adhesive bond between two substrates comprising:
   a dispenser adapted to supply an adhesive to a first of said substrates at a dispensing station;
   a conveyor adapted to convey said first substrate from said dispensing station to a compressing station within an open time period of preselected duration, said open time period commencing after application of said adhesive to said first substrate;
   a vertically movable tension head holding a second of said substrates adjacent said compressing station;
   a compression cylinder adapted to raise said first substrate into contact with said second substrate and to apply a preselected substantially constant compressive force to said substrates during a compression time period of preselected duration to form an adhesive bond therebetween, said compression time period commencing after the lapsing of said open time period;
   a vertically movable slide supporting said tension head and adapted with said compression cylinder to cooperatively raise said bonded substrates upwardly through a transition distance at a substantially constant rate of speed, said compression cylinder continuing to compress said bond under said substantially constant force during said cooperative raising;
   a stop plate located above said transition distance and adapted to engage and to prevent further upward movement of said first substrate at the end of said compression time period, said second substrate continuing to be raised upwardly by said slide at a substantially constant rate of speed to break said adhesive bond; and
   a load cell connected to said tension head and adapted to measure a maximum tensile force required to break said adhesive bond.

10. The apparatus of claim 9 wherein said conveyor further comprises:
    two endless motor-driven belts spaced apart to provide an open space directly beneath said dispenser, thereby to prevent accidental application of said adhesive to said conveyor.

11. The apparatus of claim 9 wherein said load cell also provides a real time analog output signal for the pull force of the bond during tension, whereby said signal may be utilized to obtain a measurement of the total work expended in breaking the bond.

12. The apparatus of claim 9 wherein said tension head further comprises:
    means for engaging opposite end portions of said second substrate and tensioning a midportion between said end portions to hold said midportion firmly against a horizontal bottom surface of said tension head; and
    means for retaining said engaging and tensioning means to assure that said midportion is held securely to said bottom surface during compression and tension on the bond.

13. A method for measuring the bonding strength of an adhesive comprising the steps of:
    applying the adhesive to a first substrate;
    forming an adhesive bond between said first substrate and a second substrate by applying a substantially constant compressive force to said substrate;
    pulling one of said boned substrates from the other of said substrates at a substantially constant rate of speed to pull apart said adhesive bond; and
    measuring the pull force applied to said adhesive bond during said withdrawing step.

14. The method of claim 13 and further comprising the step of:
    recording a maximum measured pull force.

15. The method of claim 13 wherein said adhesive bond is formed between substantially horizontally oriented surfaces of said substrates and said bond is pulled apart by pulling one of said bonded substrates away from the other of said substrates in a vertical direction, thereby to measure a pull force required to break said bond.

16. The method of claim 13 wherein said substantially constant compressive force is applied for a compression time period of preselected duration, said compression time period ending upon the commencement of said pulling step.

17. The method of claim 13 wherein said forming step is performed after the lapsing of an open time period of preselected duration, said open time period commencing upon completion of said applying step.

18. The method of claim 13 and further comprising the step of:
    moving said substrates through a transition distance at a substantially constant rate of speed during a portion of said forming step.

19. The method of claim 13 and further comprising the step of:
    recording a real time analog output signal for the pull force of the bond throughout said pulling step, and utilizing said signal to obtain a measurement of the total energy expended in breaking the bond.

20. A method of measuring the bonding strength of an adhesive comprising the steps of:
    (a) applying an adhesive to a first substrate during a preselected time period;
    (b) forming an adhesive bond between said first substrate and a second substrate by applying a preselected substantially constant compressive force to said substrates during a compression time period of preselected duration, said compression time period commencing after the lapsing of an open time period of preselected duration, said open time period commencing upon completion of said applying step;
    (c) moving said substrates through a transition distance at a substantially constant rate of speed during a latter portion of said forming step;
    (d) pulling one of said bonded substrates away from the other of said substrates at a substantially constant rate of speed to pull apart said adhesive bond after said compression time period, said other of said substrates being restrained from movement in said first direction; and
    (e) measuring the maximum pull force of said adhesive bond during said withdrawing step.

21. The method of claim 20 further comprising the step of:
    displaying said preselected open time period, said preselected compression time period and said maximum measured pull force.

22. The method of claim 20 further comprising the step of:

recording the preselected open time period, said preselected compression time period and said maximum measured pull force.

23. The method of claim 20 further comprising the step of:
for a selected adhesive, repeating steps a) through (e) for various different, preselected compression time periods under a constant preselected compressive force, thereby to obtain a relationship between maximum measured pull strength of the bond versus compression time for the selected adhesive.

24. The method of claim 20 further comprising the step of:
for a selected adhesive, repeating steps (a) through (e) for various different, preselected open time periods under a constant compressive force, thereby to obtain a relationship between maximum measured pull force of the bond versus open time for the selected adhesive.

25. The method of claim 20 and further comprising the step of:
providing a real time analog output signal for the pull force of the bond throughout said withdrawing step, and utilizing said signal to obtain a measurement of the total energy expended in breaking the bond.

* * * * *

UNITED STATES PATENT AND TRADEMARK OFFICE
CERTIFICATE OF CORRECTION

PATENT NO. : 4,893,513
DATED     : January 16, 1990
INVENTOR(S) : Schroeder et al.

It is certified that error appears in the above-identified patent and that said Letters Patent is hereby corrected as shown below:

In the Abstract, line 16, delete "costant" and insert
-- constant --

Column 1, line 12, delete "laps" and insert --flaps--

Column 8, line 20, delete "hold circuit in the amplifier"
and insert -- hold circuit in the load cell amplifier --

Column 12, line 1, delete "boned" and insert --bonded --

Column 13, line 6, delete a) and insert -- (a) ---

Signed and Sealed this

Eleventh Day of December, 1990

Attest:

HARRY F. MANBECK, JR.

*Attesting Officer*     *Commissioner of Patents and Trademarks*